United States Patent [19]
Hutchinson

[11] Patent Number: 5,929,972
[45] Date of Patent: Jul. 27, 1999

[54] COMMUNICATION APPARATUS AND METHOD FOR PERFORMING VISION TESTING ON DEAF AND SEVERELY HEARING-IMPAIRED INDIVIDUALS

[75] Inventor: Ray Anthony Hutchinson, Olivenhain, Calif.

[73] Assignee: Quo Vadis, Inc., Encinitas, Calif.

[21] Appl. No.: 09/007,006

[22] Filed: Jan. 14, 1998

[51] Int. Cl.⁶ ..................................................... A61B 3/02
[52] U.S. Cl. ......................... 351/237; 351/243; 351/246; 351/200
[58] Field of Search .................................. 351/205, 200, 351/243, 239, 237, 227, 222, 246

[56] References Cited

U.S. PATENT DOCUMENTS

| | | | |
|---|---|---|---|
| 3,651,512 | 3/1972 | Summers | 340/286 |
| 4,239,351 | 12/1980 | Williams et al. | 351/211 |
| 4,406,998 | 9/1983 | Willough | 340/815.01 |
| 4,906,998 | 3/1990 | Lewis | 351/239 |
| 5,129,720 | 7/1992 | Jovicevic | 351/243 |
| 5,692,906 | 12/1997 | Corder | 434/156 |
| 5,694,199 | 12/1997 | Rodriquez | 351/239 X |

OTHER PUBLICATIONS

Wood, Theresa "Communicating with Hearing–Impaired Patients" Journal of the American Optometric Association, vol. 58, No. 1, Jan. 1987 pp. 62–65 American Optometric Association, St. Louis.

Marino, Donna "Managing the Hearing–Impaired" Optometric Management, vol. 24, No. 10, Oct. 1988, pp. 67–71 Boucher Communications, Inc., Norwalk, CT.

*Primary Examiner*—Huy Mai
*Attorney, Agent, or Firm*—Frank D. Gilliam

[57] ABSTRACT

An apparatus and method for communicating to a deaf or severely hearing impaired individual while vision testing utilizing indicator lights (52A), (52B), (52C), and (52D) positioned in the same plane as a visual acuity test chart (54) having optotypes (50B). The examiner activates the indicator lights by means such as an infra-red remote control receiver (56). This is done in a manner previously disclosed to the examinee permitting the examinee to understand messages from the examiner, while the examiner simultaneously operates a refractor to determine the refractive state of the examinee.

9 Claims, 7 Drawing Sheets

COMMUNICATION APPARATUS AND METHOD FOR PERFORMING VISION TESTING ON DEAF AND SEVERELY HEARING-IMPAIRED INDIVIDUALS

BACKGROUND

1. Field of Invention

This invention relates to vision testing deaf or severely hearing-impaired individuals, specifically to the means by which the examiner communicates the necessary instructions to the hearing impaired individual during the course of the examination.

2. Description of Prior Art

The usual means of communicating to deaf and hearing-impaired individuals are through the printed word, sign language, finger spelling, lip reading, gestures or by touch. Except for touch, the hearing-impaired individual must be able to observe the one attempting the communication. Other means of non-verbal communication for the handicapped have been developed. U.S. Pat. No. 4,406,998 to Willough, Sep. 27, 1983 discloses a device which allows communication through lighted message blocks. Many devices have been developed which allow communication from a handicapped person to another, such as the apparatus disclosed in U.S. Pat. No. 3,651,512 to Summers, Mar. 21, 1972.

A vision examination consists of many parts. Typically, an eye examination will include the patient case history, visual acuity testing, various eye health tests, muscle balance tests, objective refraction and subjective refraction. Visual acuity testing is accomplished using various types of visual acuity test targets and displays. A test distance between the patient and the test targets is typically twenty feet. Visual acuity test targets are known as optotypes. One such optotype is disclosed in U.S. Pat. No. 4,968,131 to Lewis, Nov. 6, 1990. Historically these test targets were presented to the patient as a wall chart having the optotypes imprinted on it. Currently, the most common method of presenting the optotypes to the patient is through the use of a chart projector which projects the optotypes upon a reflective screen. To permit adequate visualization of the projected acuity chart, the room is generally made dark. Alternative methods of displaying visual acuity charts have been developed. One such device is a translucent panel with imprinted optotypes which is rear-illuminated as disclosed in U.S. Pat. No. 5,129,720 to Jovicevic, Jul. 14, 1992. Another method employs a computer to generate optotypes upon a video display unit as disclosed in U.S. Pat. No. 4,239,351 to Williams, et al, Dec. 16, 1980. Testing of visual acuity and the use of optotypes is integral to the vision examination and is measured repeatedly during the subjective testing phase of the examination.

For most of the examination, the examiner is face-to-face with the patient. The examiner may communicate to a hearing-impaired patient during the case history and eye health tests with relative ease. This can be accomplished through printed material, lip reading or, if the examiner is so skilled, sign language or finger spelling. Alternatively, the examiner may use a sign language interpreter who must also be within the patient's view. It is when a deaf patient is positioned behind a refractor that difficulty arises in performing the vision examination.

A refractor is an optical device containing many lenses through which the patient looks at a visual acuity display. A refractor is also known as a phoropter. The lenses of a refractor may be selected to be presented to the patient individually or in combination. Besides lenses for determining the patient's refractive state, there are various lenses and devices for measuring the patient's extra-ocular muscle balance. Also, wheels and mechanisms for moving the lenses. In order to contain all of the necessary lenses, refractors are not small. Newer types of automated refractors are even larger as they must contain added machinery and electrical components to automatically position the lens combinations in front of the patient. A refractor covers at least the upper half of a patient's face, and extends several inches to either side of the face. It is very difficult for a patient to look around or to the side of a refractor. Often, a patient's head movement is further restricted by a headrest on the examination chair. The refractor has a very restricted field of view through the lens apertures. Little else besides the acuity chart is visible to the patient. As the room is generally dark, this further impedes the patient's ability to visualize anything besides the acuity chart. Once positioned behind a refractor, the hearing-impaired patient has been effectively cut off from further visual communication from the examiner or the interpreter.

Typically, to perform a subjective refraction, the examiner presents to the patient various sets of lens combinations through the refractor. The patient is asked to choose which lens combination out of a set of choices gives the better focus. Using that information, the examiner presents another set of choices. Usually, the initial choices will show a distinct difference between them. As the examination progresses and the examiner is closer to determining the patient's glasses prescription, the difference between the choices becomes more subtle. Often, unless alerted through another clue, a patient may be unable to recognize that a different lens combination has been presented.

During this subjective refraction process, the examiner needs to find out how well the patient is seeing through a particular lens combination. The patient is asked to read the letters on the acuity chart. If the patient can read the letters of a particular size, the examination can then continue with letters of a smaller size. This process continues until the examiner is satisfied that no other lens combination will allow the patient to read smaller letters.

From this discussion, it is apparent that the examiner must communicate to the patient. The examiner must be able to indicate that the patient is about to be shown a set of lens choices. Then the examiner must be able to label each choice (e.g. choice one or choice two). This label must be able to be maintained through several presentations of the same set of choices to allow the patient a more thorough evaluation of each choice. The examiner needs to be able to indicate that a different set of choices is about to be presented to repeat the cycle. Finally, the examiner needs to be able to demand a response from the patient—either to make a choice of the presentations or to read aloud the letters presented.

Currently, there are not any satisfactory means for communicating with the hearing-impaired individual during a subjective refraction. Those methods now employed by vision examiners are as follows:

a) The examiner may position the patient behind the refractor, and by waving his or her hand in front of the fine of sight of the patient, attempt communication. This method is unsatisfactory for several reasons. The communication becomes ambiguous and confusing. The examiner may not flag the examinee in exactly the same way each time so the patient can easily become confused and unsure of the given signal. The examiner's hand may momentarily obscure the view of the visual acuity chart which also is distracting and confusing to the patient. Also, the patient may change focus from the acuity chart, which is set at a particular test distance, to the examiner's hand which would only be a very short distance in front of the patient. This change of focus with the need to then refocus to the distance of the acuity chart may cause inaccurate results in the measurement of the patient's refractive state.

b) The examiner may not perform a subjective refraction at all. Instead, the examiner may only use the information from the objective refraction to prescribe the vision correction. Objective refraction is a method whereby the examiner uses various means to measure the patient's refractive state without feedback from the patient. Retinoscopy and automated refractors are examples of objective refraction. Even the most sophisticated objective refraction technique is not, at present, as accurate a method of determining a patient's refractive state as subjective refraction. In some instances, objective refraction is completely inaccurate and must be entirely disregarded, as shown through the patient's responses in a subjective refraction. Elimination of the subjective refraction is a very poor answer to the communication hardships presented by deaf and hearing-impaired individuals.

c) Another solution used by examiners is to not use a refractor but to use a special glasses frame (known as a trial frame) that allows the insertion of loose trial lenses by hand. Since this special frame allows the free movement of the patient's head and the field of view is less restricted, the examiner can remain within the patient's view. However, this trial frame method is very time consuming. The frame must be continually removed from the patient's face and the loose lenses changed by hand. It is difficult to quickly present alternative choices. Special refractive procedures such as a Jackson crossed cylinder test become difficult and less accurate when using a trial frame versus a refractor. Using a trial frame is time-consuming, cumbersome, and less accurate.

d) Lastly, a means of communicating to a hearing-impaired patient while using a refractor is through touch. The patient's knee or shoulder can be touched by the examiner to indicate different choices, or to indicate the need for a response. This method is unsatisfactory as it requires the examiner to come into physical contact with the patient. Many individuals feel uncomfortable with forced physical contact. To some extent, such touching undermines the dignity of the individual. It could even provide an opportunity for inappropriate touching of the patient by the examiner. Also, only a very limited amount of information can be transmitted through touch. While this means of communication can and does work, a superior method of visual communication is wanting.

OBJECTS AND ADVANTAGES

Accordingly, the object of this invention is to provide a means of communicating to a deaf individual, or someone with severe hearing loss, while at the same time providing for the display of a visual acuity chart to facilitate vision testing while using a refractor. There are numerous other objects and advantages of the present invention:

a) to provide a means for a vision testing examiner to communicate effectively to a deaf or hearingimpaired individual during testing using a refractor;

b) to provide a means for communication to a deaf or severely-hearing impaired individual who may also be visually impaired and as such, unable to read printed messages that may be displayed at the usual vision test distance of twenty feet;

c) to provide a means for communication to the hearing-impaired which allows subjective refraction to be conducted with a refractor such that the refraction is faster and more accurate for the patient;

d) to provide a means of communication to the hearing-impaired patient which is precise and unambiguous during subjective refraction testing;

e) to provide a means of communicating to a deaf or hearing impaired person while conducting any other vision tests using a refractor such as phoria or vergence muscle balance testing;

f) to provide a means of communicating to a deaf or hearing impaired individual which maintains the focus of the examinee at the proper test distance without requiring change of focus to and from a signaling device.

g) to provide a means of visually communicating to a deaf or hearing impaired individual while conducting a vision test in a darkened room;

h) to provide a means of communication to the deaf or hearing-impaired which maintains their dignity as a person while testing their vision using a refractor;

i) to provide a means of effectively communicating to the deaf and hearing-impaired during subjective refraction testing and other vision tests such that their most important sense of sight is maximized.

Further objects and advantages are to provide to the deaf and hearing-impaired individual a sensation of understanding and capability while having their vision tested, rather than feelings of embarrassment, confusion, doubt, and worry that they are not responding in the way expected by the examiner. Still other objects and advantages will be appreciated through study of the subsequent description and drawings.

SUMMARY

The current invention is an apparatus, and method, for communicating to deaf or severely hearing-impaired individuals comprising: a visual acuity chart combined with indicator lights, which the examiner can activate to transmit messages to the individual whose vision is being examined with the use of a refractor.

Code (See Appendix 1)

Illustrative code, written in C programming language is provided as in Appendix 1 hereto.

DETAILED DESCRIPTION

The following description is of four embodiments of the present invention. One embodiment is significantly different in structure from the other three, yet each serve to demonstrate the general concept of the invention. The four embodiments should not be taken as limiting the scope of the invention. Rather, the dimension of the invention should be determined through appreciation of the claims.

Figure 1:
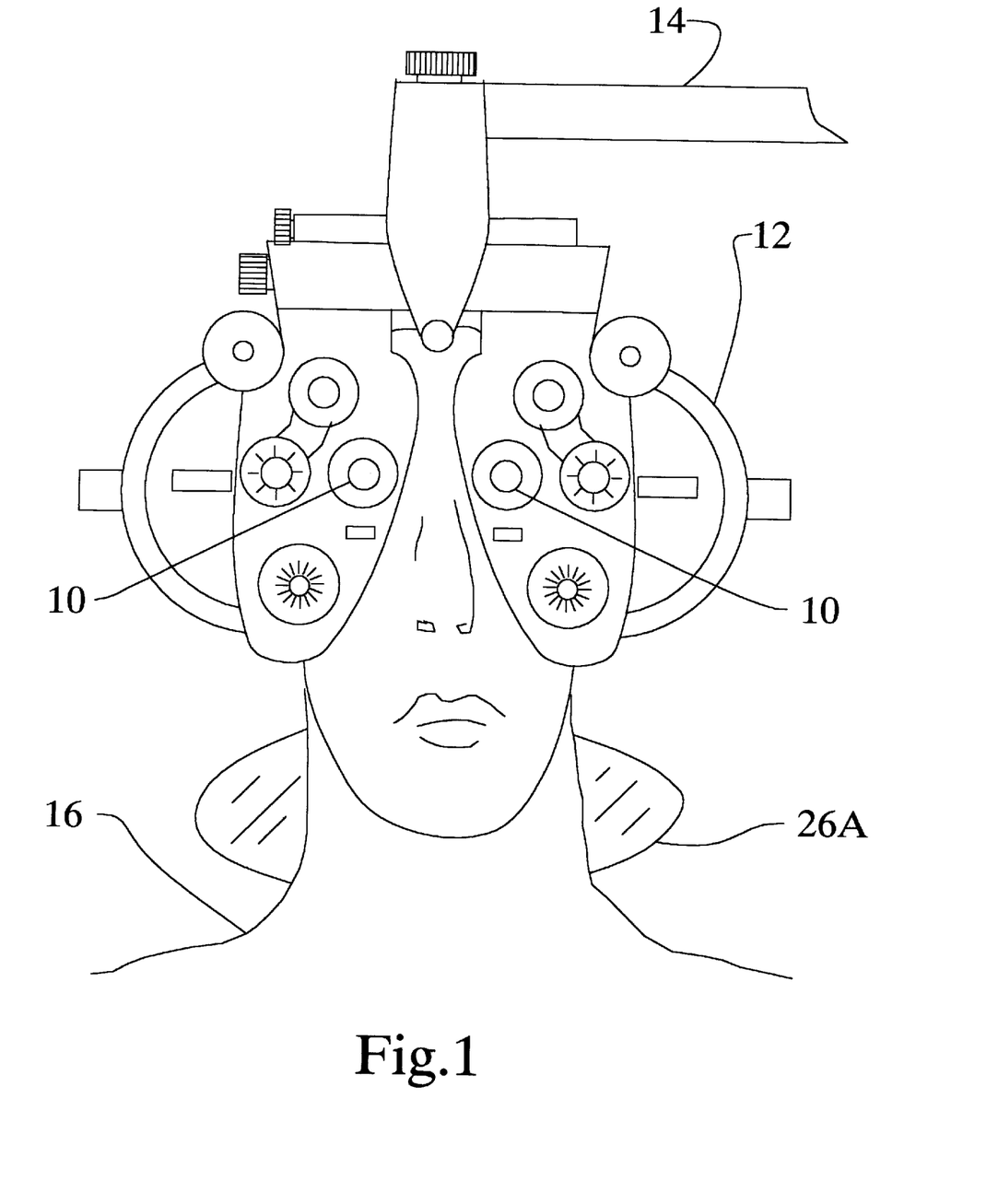
FIG. 1 is a front view of a typical refractor positioned in front of a patient.
Figure 2:
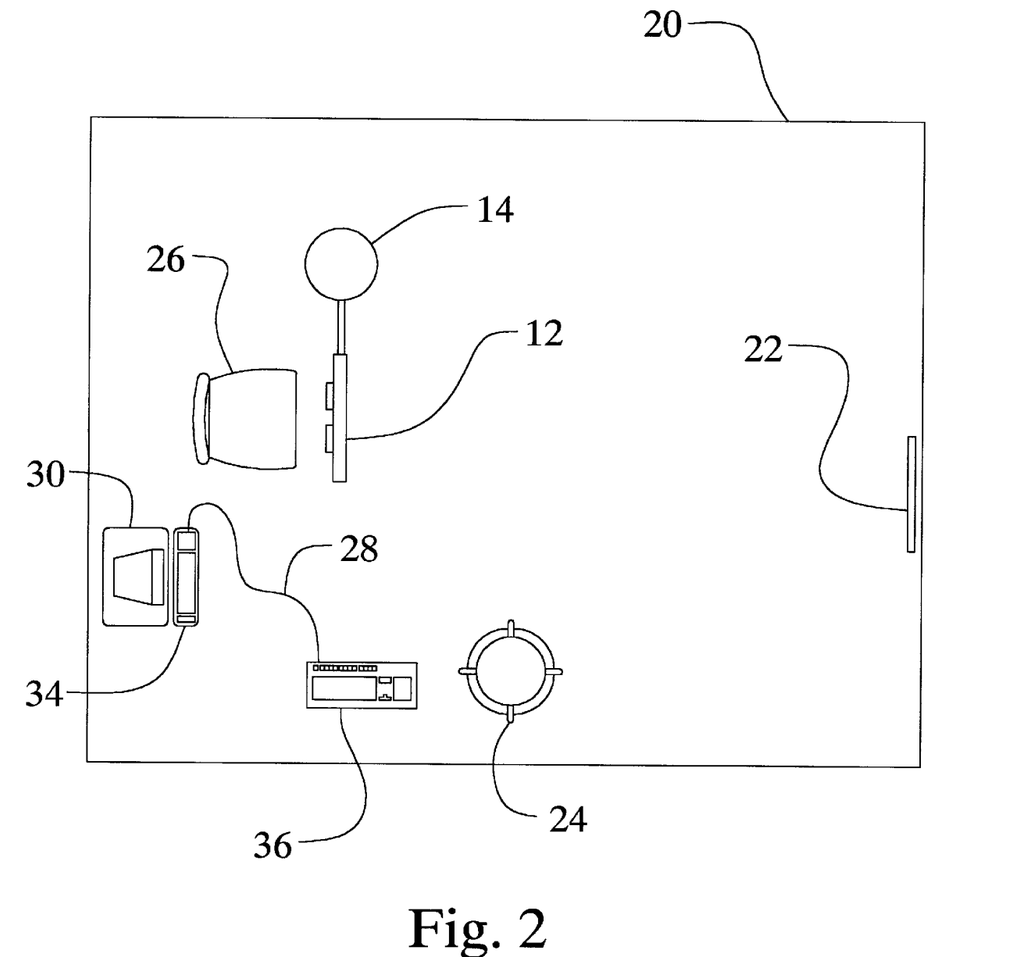
FIG. 2 is a top plan view of a typical examination room showing the present invention in relation to the examination chair, the refractor, and the examiner.

Referring to FIG. 1, a typical refractor 12 is positioned as in a clinical testing situation in front of the face of a patient 16. The refractor is mounted on a supporting arm 14. A headrest 26A is positioned behind the patient. The patient looks through apertures 10 of the refractor while the examiner manipulates the various dials and controls of the refractor to position lenses within the apertures. FIG. 2 depicts a usual examination room 20. Situated within the room an examination chair 26 for the patient, a stool 24 for the examiner, and refractor 12 is mounted on supporting arm 14. As is common practice, a mirror 22 is positioned at one end of the room to reflect the image from a computer display 30 through the refractor to the patient seated in chair 26. Such a reflection system allows a smaller size room to provide the necessary test distance of approximately 20 feet. A keyboard 36 is positioned near the examiner and is connected to a computer 34 by means of a cable 28.

Figure 3:
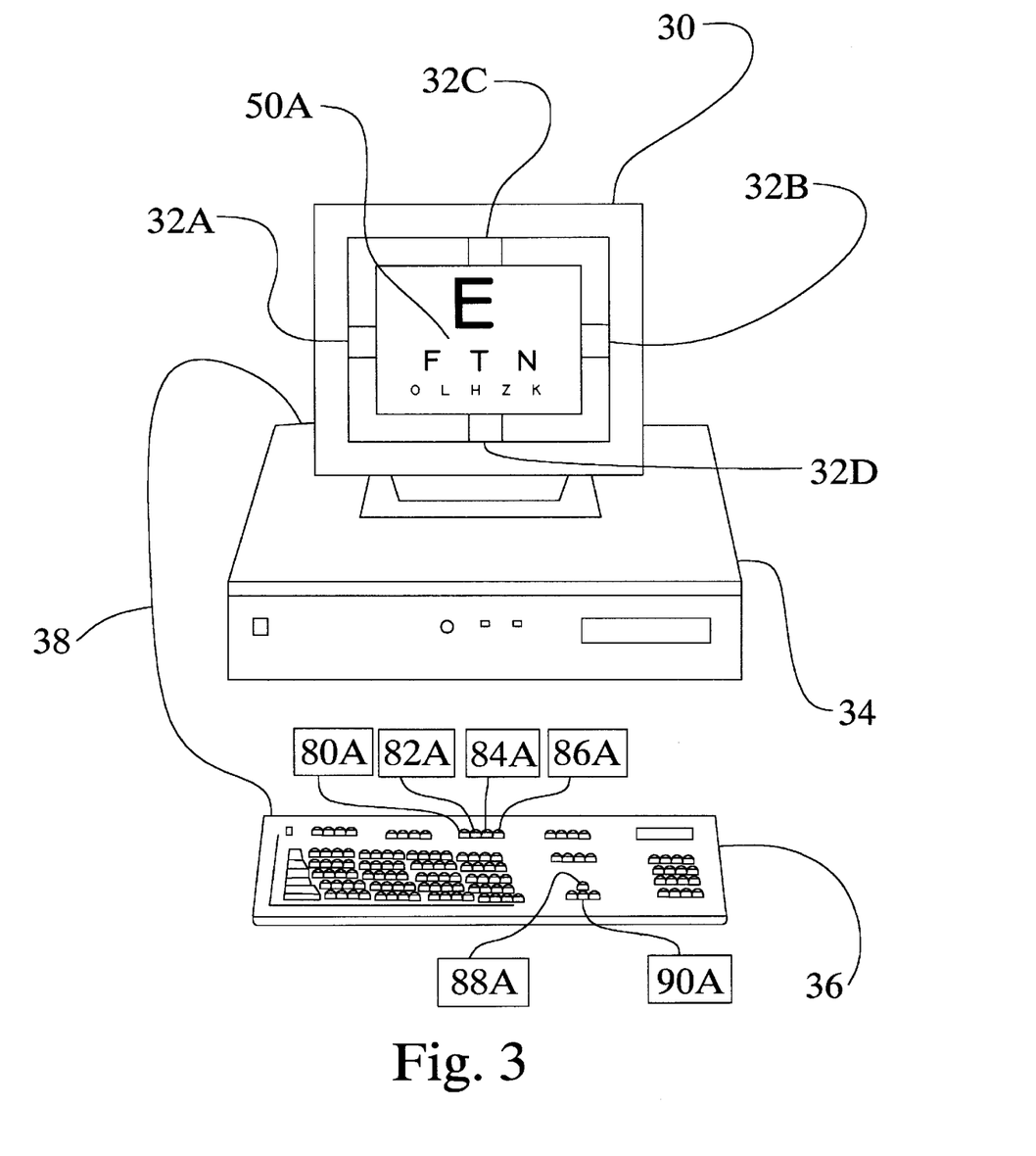
FIG. 3 is a depiction of one embodiment of the present invention wherein the visual acuity chart and the indicator lights are displayed on a computer video display.

FIG. 3 illustrates one embodiment of the invention. It depicts a digital computer 34 attached to a display unit 30 which can display a plurality of optotypes 50A, while at the same time allowing a plurality of individual indicator lights 32A, 32B, 32C, and 32D to be activated singly or in combination. A variety of optotypes and sizes of optotypes are envisioned for the preferred embodiment of the invention. The optotypes shown are for illustrative purposes only.

In the preferred embodiment, the indicator lights are all of one color, having a wavelength approximately in the middle of the visual spectrum, and are positioned to each side, the top, and the bottom of the visual acuity optotype display. The preferred wavelength will produce a yellow-green color. Such an indicator light arrangement would preserve the focus of the examinee to the visual acuity optotypes. Using various colors as indicator lights, or wavelengths at the extremes of the visual spectrum, could have an unwanted effect on the state of accommodative focus of the examinee producing inaccurate refractive error measurements. However, an examiner may have reason to purposefully alter the examinee's state of focus. Also, the positioning of the indicator lights to the sides, top, and bottom shown in the preferred embodiment could easily be arranged in an alternative manner, and more or less in number. Therefore, the preferred embodiment of four single wavelength indicator lights in the middle of the visual spectrum positioned as shown in FIG.3 should not be considered as a limitation of the present invention.

The computer has an input device of a keyboard 36. A typical keyboard has an F9 key 80A, an F10 key 82A, an F11 key 84A, and an F12 key 86A. Keyboards also have an up-arrow key 88A, and a down-arrow key 90A. It should be observed that computers can have numerous methods of inputting control instructions. Other forms of input include, but are not limited to, microphones permitting voice input, mouse pointers, trackballs, light pens, infrared keyboards, et cetera. While this present embodiment uses a keyboard for input, the scope of the invention should not be limited to this input device.

Figure 4:
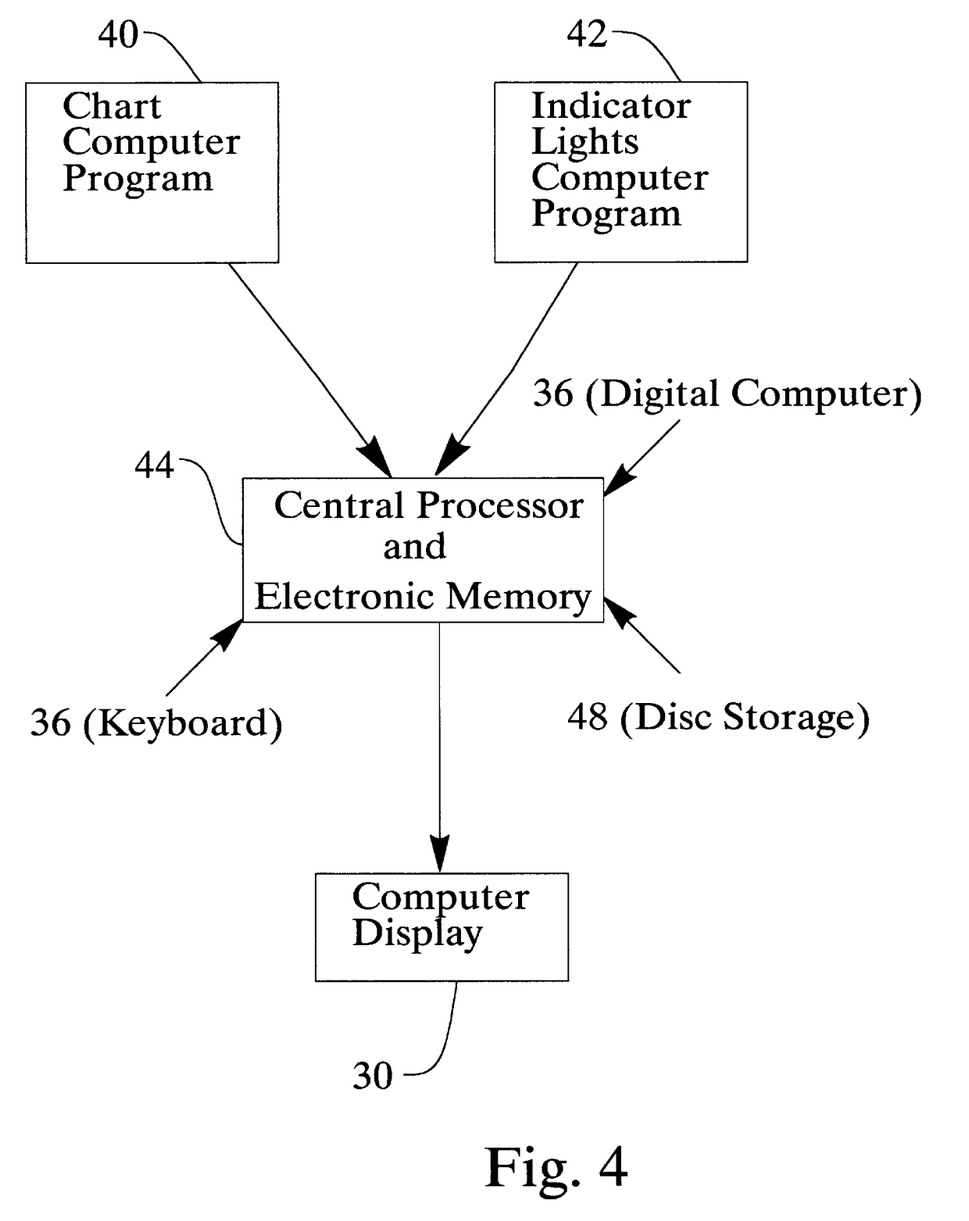
FIG. 4 is a block diagram of the system of FIG. 3.

FIG. 4 is a block diagram of the system illustrated in FIG. 3. A central processor with an electronic memory 38 is activated by the digital computer 34. The central processor receives instructions from two programs—a visual acuity chart program 40, and an indicator lights program 42. These programs reside either within the digital computer memory and central processor, or in a storage device such as a diskette or a hard disc 48. Input to the central processor is via a keyboard 36, while the output is to a computer video terminal display 30.

APPENDIX 1 is a listing of programs 40 and 42. The code is written in the C Programming Language. The program may be run on an IBM™ compatible computer having at least a 80386 processor, 4 megabytes of random access memory, a VGA graphics card adapter, a VGA monitor, DOS 5.0™ operating system or above as the operating system, and a Borland™ C compiler or a compatible equivalent. The method of compiling, linking, and executing this source code is conventional and well known to those skilled in the art. This code when executed will produce programs 40 and 42. It should be realized that other programs written in a variety of programming languages and used on different computer configurations can be made to function in a like manner to the source code of APPENDIX 1. Such embodiments are entirely acceptable and wholly equivalent.

Figure 5:
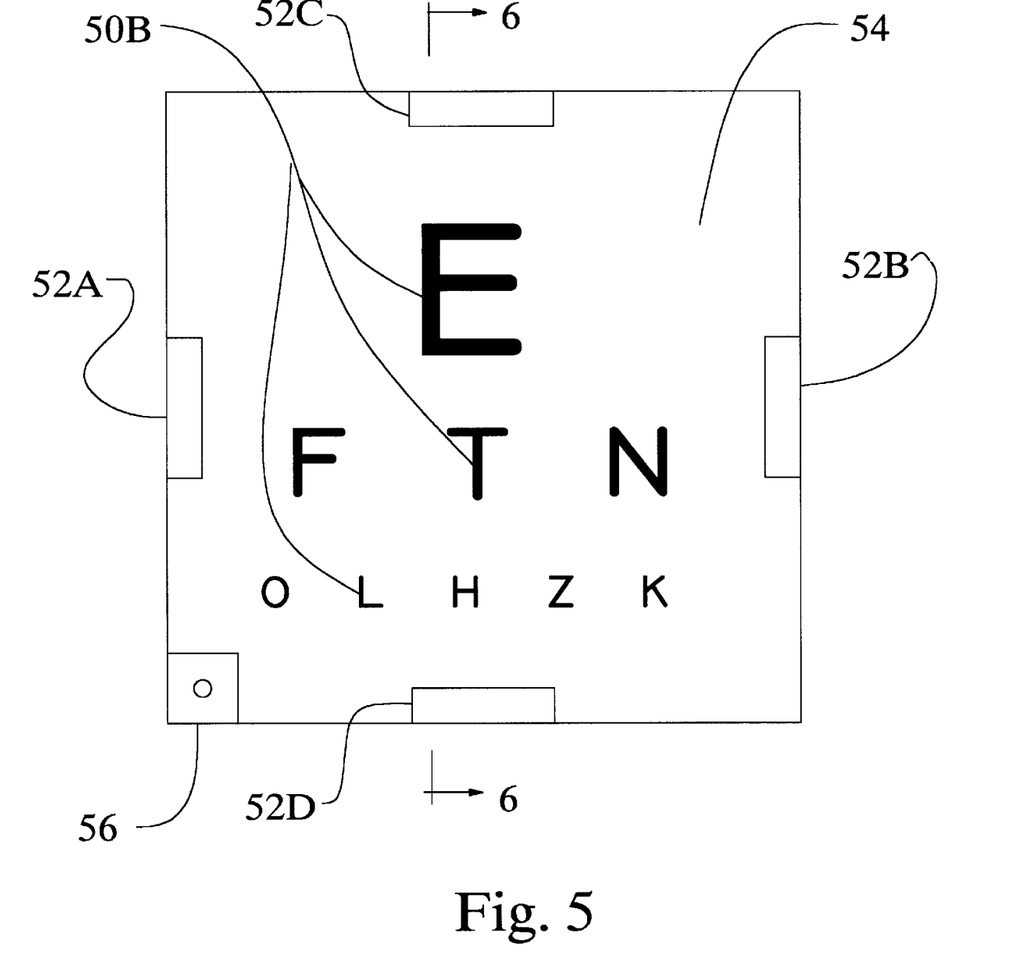
FIG. 5 is a front view representing three alternate embodiments each having identical front appearances.

FIG. 5 depicts a front view of three alternate embodiments A, B, and C of the present invention. Individual indicator lights 52A, 52,B 52,C and 52D are positioned at the sides, top, and bottom of a visual acuity optotype display 54. They can be singly or in combination activated through an infra-red receiver 56. The indicator lights are positioned in the same plane as the visual acuity optotypes, so that the visual focus of the examinee does not vary when changing their point of regard from the visual acuity chart to the indicator lights. As previously discussed with FIG. 3, the number and plait of the indicator lights can be changed without affecting the principle behind the present invention. The infra-red receiver and its circuitry, and the circuitry from the receiver to the indicator lights are of conventional design. Such design and its implementation are well known and understood by those skilled in the art and need not be described in detail here. The front surface of the visual acuity chart 54 differs for embodiments A, B, and C. In embodiment A, the front surface is a reflective surface to reflect light from a visual acuity chart projector producing a plurality of optotypes 50B. For embodiment B, the front surface is a printable surface upon which are printed optotypes 50B to create the visual acuity chart. Embodiment C uses a translucent material which allows light to pass through it from the rear, except where the optotypes have been imprinted, thus permitting viewing of the acuity chart from the front.

Figure 6A:
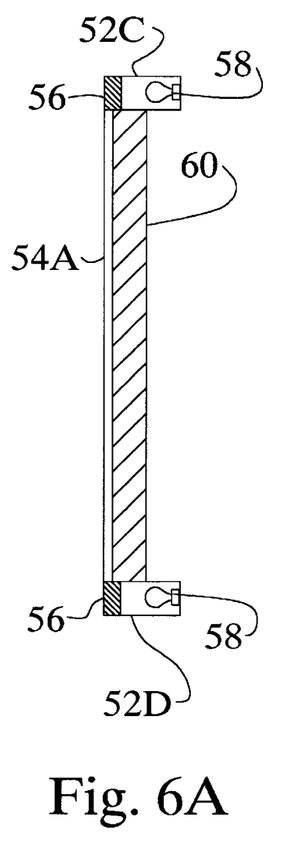
FIGS. 6A, 6B, and 6C are cross-section views of the three alternate embodiments of the apparatus of FIG. 5 along the line 6—6 of FIG. 5.
Figure 6B:
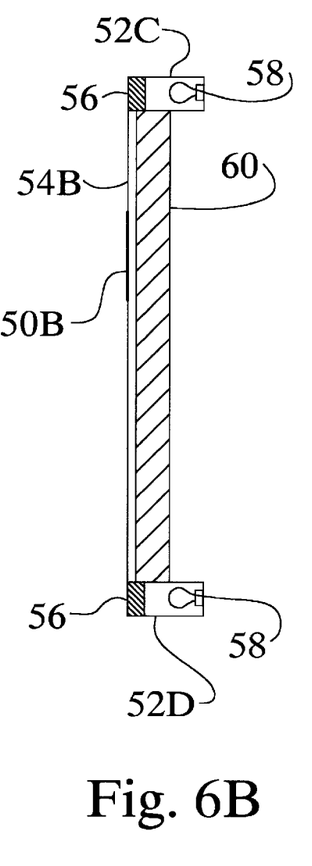
Figure 6C:
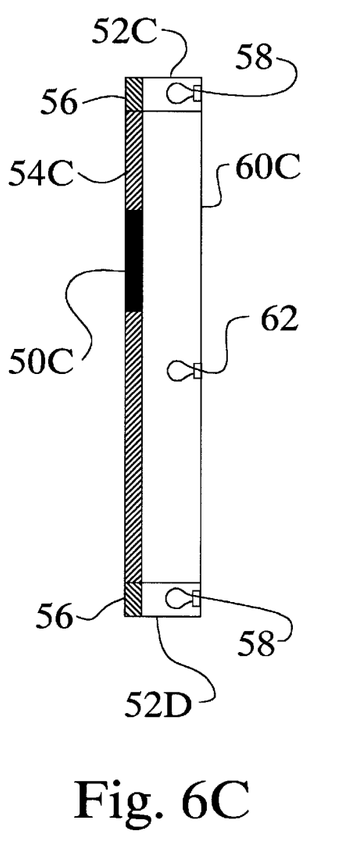

FIGS. 6A, 6B, and 6C are cross sections of FIG. 5 through the line 6—6. FIG. 6A shows a reflective front surface 54A. Many substances can be used to produce the reflective surface such as reflective metal or reflective silver colored paint. Supporting this front service is a backing substrate 60. This backing also can be made out of numerous substances such as plywood or particle board. Indicator lights 52C and 52D have a plastic translucent cover 56 permitting only yellow-green light to pass through from an incandescent light source 58. The side indicator lights which are not shown in these sections are of the same structure as 52C and 52D. As previously discussed, this represents the preferred embodiment for the indicator lights although alternative light arrangements are possible. FIG. 6B differs from FIG.6A only in regard to front surface 54B which is a printable surface such as heavy white paper. Segments of the optotype are seen at 50B. The front surface of FIG. 6C is translucent white plastic with optotype 50C impregnated in the plastic. A plastic housing 60C contains an incandescent light source 62 to produce rear lighting of the translucent front surface. The indicator lights of FIG. 6C are the same as FIG. 6A.

Figure 7:
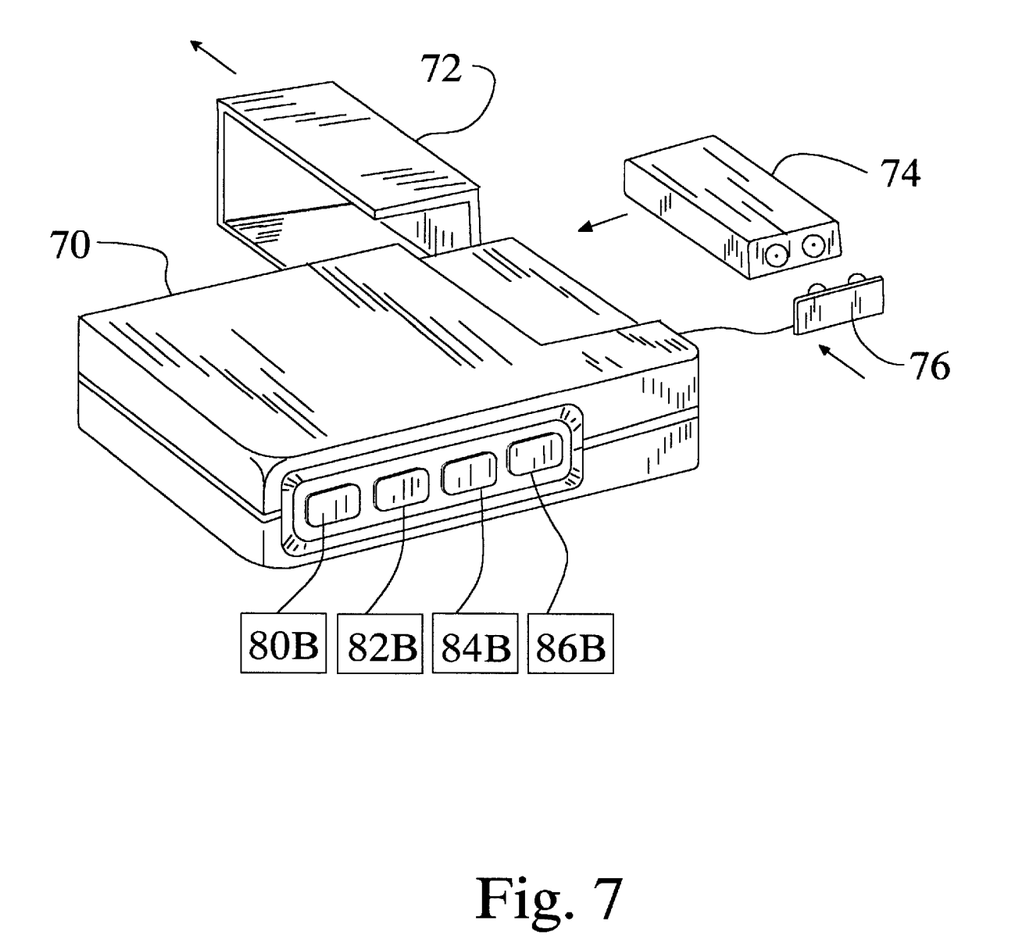
FIG. 7 is a perspective view of a remote control unit for utilization with the apparatus of FIG.5.

FIG. 7 is a perspective view of an infra-red remote control 70 for selectively activating the indicator lights of FIG. 5. The unit has a removable side 72 to allow for insertion of a conventional battery 74. The battery is connected to the unit via a snap on connector 76. The unit has a set of four buttons for operation 80B, 82B, 84B, and 86B. As with the infra-red receiver unit of FIG. 5, the remote control unit is of conventional design and implementation. This is well known and understood by those skilled in the art and does not need further detail here. Many alternative methods of controlling the indicator lights are possible, such as control wires, radio control, et cetera. The present embodiment of infra-red remote control is preferred for convenience of operation, but should not be regarded as limiting the control method for the present invention.

Operation

Referring to FIG. 7, buttons 80B, 82B, 84B, and 86B activate the indicator lights of FIG. 5 in the following manner. Depressing button 80B causes the left side indicator light to turn on. Pushing button 80B a second time turns off any and all indicator lights which are currently activated. Depressing button 82B turns on the left side light while simultaneously turning off the right side indicator light. Repeated operation of button 82B toggles between activating one of the side lights while simultaneously deactivating the other side light. Button 84B turns the top indicator light on and off Button 86B turns the bottom indicator fight on and off.

To use the invention, the examiner first describes to the deaf or severely hearing impaired patient the messages to be conveyed through the indicator lights. This is done before the patient is positioned behind the refractor and can be explained through printed information, lip reading, signing or any other visual form of communication. Once the patient understands the meaning of the indicator lights, he or she is positioned behind the refractor as in FIG. 1. If the visual acuity optotype chart is as described in FIGS. 6A and 6C, the examiner turns on the acuity chart. The examiner chooses a lens combination of the refractor to place in front of one of the patient's eyes. At this time the examiner depresses button 80B to turn on the left side indicator light. The patient understands from this indicator light that lens combination one is now in place. The examiner next positions lens combination two in front of the patient's eye and simultaneously depresses button 82B. This turns off the left side light and turns on the right side light. The patient understands that lens combination two is now in place. The examiner can switch between the two lens combinations while at the same time depressing button 82B to toggle the indicator lights between choices one and two. After sufficient presentations of the lens combinations, the examiner depresses button 84B which turns on the top indicator light. The patient understands that the examiner is now asking for a choice of which lens combination is better, one or two. To this the patient verbally, or in some manner, indicates which lens choice, one or two, is clearer. The examiner then depresses button 80B again. This turns off all the lights and indicates to the patient that a new set of lens choices is about to be shown. The process is then repeated with the examiner placing another lens combination in front of the eye and depressing button 80B again to turn on the left side light. As needed throughout the examination, the examiner depresses button 86B which activates the lower indicator light. To this light the patient knows to read the line of optotypes to the examiner. The process is continued in the usual manner of determining a patient[\M]s refractive error.

The operation of the embodiment of FIG. 3 is similar to that just described except that keys on the keyboard are used in place of the buttons of FIG. 7. Referring to FIG. 3, 80A toggles on and off left indicator light 32A; 82A toggles on and off right indicator light 32B; 84A toggles on and off bottom indicator light 32C; and 86A toggles on and off top indicator light 32D. Up-arrow key 88A increases the size of optotypes 50A Down-arrow key 90A decreases the size of the optotypes.

The described method of operation is one of many possible. An examiner can tailor the messages transmitted by the indicator lights to their own needs and preferences in performing a vision examination. The detail of operation is for illustrative purposes and should not limit the scope of the present invention.

Conclusion, Ramifications, and Scope

Accordingly, it is apparent that the present invention provides a useful means of communication from a vision examiner to a deaf or severely hearing-impaired individual while that individual is positioned behind a refractor. A person handicapped by the loss of their sense of hearing must rely heavily on their other senses, especially their most valuable vision sense. It is imperative that this precious sense be maximized to its fullest potential. The present invention provides advantages to the vision examiner so that they may more readily assist the deaf and severely hearing-impaired achieve maximal vision.

While the above description of the four embodiments and the method of operation of the present invention contain many specificities, these should not be construed as limiting in scope. Rather, these specifications should be understood to be illustrative in nature of these particular embodiments of the invention. For example, the indicator lights are shown to be incandescent light fixtures. Many other forms of light arrangements are possible such as light emitting diodes, halogen lights, fiber optic light, flashing lights, et cetera. The examination room arrangement indicates a mirror to provide a smaller room while maintaining a usual test distance of twenty feet. Other optical systems could be employed to achieve an equivalent test distance. The method of controlling the indicator lights of all the present embodiments use depressing buttons. Altenative methods of control could be voice recognition software such that the examiner speaks "one or two" to toggle between indicator lights, or the use of knobs instead of buttons.

Thus, the scope of the invention should be determined by the appended claims and their legal equivalents, rather than by the examples given.

Appendix 1

```c
#include <stdio.h>
#include <stdlib.h>
/*#pragma warn -aus*/
#include <conio.h>
#include <dos.h>
#include <string.h>
#define BG 0
#define FG 1
#define U_HEIGHT 20
#define U_WIDTH 50
typedef unsigned char BYTE;
typedef unsigned char huge * u_huge;
typedef unsigned char       u_char;
typedef unsigned short    u_short;

typedef struct
{
  int x;
  int y;
  int w;
  int h;
} block_t;
typedef struct {
    int ht;   /* character height in pixels */
    int wd;   /* character width in pixels */
    int x1;
    int x2;
    int cx;   /* integral center in x direction */
    int x3;
    int x4;
    int y1;
    int y2;
    int cy;   /* integral center in y direction */
    int y3;
    int y4;
    float ut; /* one basic unit (1/4 width, 1/5 height) */
    int uw;
    int chars;
    int lw;
} shapes_t;

#define VNUM 11
shapes_t shapes[VNUM];
int Cur = 3;

float heights[ ] = { 6.52, 8.70, 11.00, 13.05, 17.40,
21.75, 26.10, 30.45,
          34.80, 43.50, 87.00 };

PAL rgb[16];

int top_on(void);
int top_off(void);
int left_on(void);
int left_off(void);
int bottom_on(void);
int bottom_off(void);
int right_on(void);
int right_off(void);
int digit1(void);
int digit2(void);
int (*toggle_top)( );
int (*toggle_bottom)( );
int (*toggle_right)( );
int (*toggle_left)( );
int (*kbfunc)( );

unsigned char clrtbl[17];

void beep2( )
{ define U_HALF_WD (U_WIDTH/2)
define U_HALF_HT (U_HEIGHT/2)
block_t top= {320-U_HALF_WD, 0,
U_WIDTH U_HEIGHT};
block_t bottom = {320 - U_HALF_WD, 480-
U_HEIGHT, U_WIDTH, U_HEIGHT};
block_t left = {0,     240-U_HALF_WD
U_HEIGHT, U_WIDTH};
block_t right = {640 - U_HEIGHT, 240-
U_HALF_WD, U_HEIGHT, U_WIDTH}, /* defaults */
unsigned int width = U_WIDTH;
unsigned int height = U_HEIGHT;
unsigned int offset = 0;
unsigned int red = 0/*128*/;
unsigned int green = 255;
unsigned int blue = 0;

typedef struct {
   u_huge addr;
   unsigned int w;
   unsigned int h;
   unsigned int lbytes;
   unsigned int mode;
} SCREEN;

SCREEN screen_params =
{(u_huge)0xa0000000,640,480,80,0x12};

void draw_chars( int v);
int setbmode( int mode);

#define ESC     0x001B /* ASCII Escape character */
#define CHAR_q      0x0051 /* ASCII character q */
#define CHAR_Q    0x0071 /* ASCII character q */
#define COLOR_INDEX 2
define WHITE 0 typedef struct Pal{
    BYTE red;
    BYTE green;
    BYTE blue;
} PAL;

typedef struct {
   unsigned char mode;
   unsigned char columns,
   unsigned char page;
} MODE2;

MODE2 mode;
   mov ah, 0fh;
   int 10h;
} columns = _AH;
   mode = _AL
   page = _BH
   omode->mode = mode;
   omode->columns = columns;
   omode->page = page;
   return(0);
}
int setpall16(unsigned char far *pall)
{
   union REGS reg;
   struct SREGS sregs;
   sregs.es = FP_SEG(pall);
   reg.x.dx = FP_OFF(pall);
   reg.h.ah = 0x10;
   reg.h.al = 2;
   int86x(0x10,®,®,&sregs);
   return(0);
}
int draw_block(block_t blk, u_char fg)
```

Appendix 1-continued

```c
    sound(350);
    delay(100);
    nosound( );
} int setpall(unsigned char far *pall)
{
    union REGS reg;
    struct SREGS sregs;
    sregs.es = FP_SEG(pall);
    reg.x.dx = FP_OFF(pall);
    reg.h.ah = 0x10;
    reg.h.al = 0x12;
    reg.x.bx = 0;
    reg.x.cx = 16;
    int86x(0x10,®,®,&sregs);
    return(0);
}
int setbmode(int mode)
{
    _AL = mode;
    asm {
        mov ah,0;
        int 10h;
    }
    return(0);
}
int getbmode(MODE2 *omode)
{
    unsigned char columns,mode,page;

asm {
        sp[0] = fg;
        sp += screen_params.lbytes;
    }
}
else if(bwidth == 1) { for(j=0;j<blk.h;++j) {

/* Firstbyte */
        mask = (0xff << left) & 0xff00;
        mask |= (sp[0]<<8);
        outport(0x3ce,mask | 0x0008); /* set plane
mask, reg 8, bit map register */
        sp[0] = fg;

/* Lastbyte */
        mask = end_mask (sp[1]<<8);
        outport(0x3ce,mask | 0x0008); /* set plane
mask reg 8, bit map register */
        sp[1] = fg;

sp += screen_params.lbytes;
    }
}
else if(bwidth = 2) {
    for(j=0;j<blk.h;++j) {

/* First byte */
        mask = (0xff << left) & 0xff00;
        mask = mask | (sp[0]<<8);
        outport(0x3ce,mask | 0x0008);
        sp[0] = fg;

/* Middle byte */
        mask = 0xff00 | (sp[1]<<8);
        outport(0x3ce,mask | 0x0008);
        sp[1] = fg;
        /* Last byte */
        mask = end_mask | (sp[2]<<8);
        outport(0x3ce end_mask | 0x0008);
        sp[2] = fg;
        sp += screen_params.lbytes;
    }
}
else {
    for(j=0;j<blk.h;++j) {
        /* First byte */

{
    u_short end,mask,end_mask;
    u_short ybyte = blk.y*screen_params.lbytes;
    u_short sbyte = ybyte + (blk.x>>3);
    u_short ebyte = ybyte + (blk.x+blk.w-1)>>3);
    u_short bwidth = ebyte - sbyte;
    u_char left = 8 - (blk.x & 7);/* (data >> count)
<<8 */
    u_char *sp = (u_char *)screen*)params.addr +
sbyte;
    u_short color_compare = (fg << 8) | 0x02;
    int ij;

end = (blk.x + blk.w) & 7;
    if(end==0)
        end_mask = 0xff00;
    else
        end_mask = 0xff00 << (8-end);

outport(0x3ce,0xf07);/* color dont care - we
care all 4 planes */
    outport(0x3ce,color_compare);
    outport(0x3ce,0xa05); /* read mode 1,write
mode 2(page 111 PC Video Systems */
    outport(0x3ce,0x003); /* rotate, raster op */ if(bwidth ==0) { for(j=0;j<blk.h;++j) {
            mask = (0xff00 >> (blk.x&7)) & 0xff00;
            mask = (mask & end_mask) | (sp[0]<<8);
            outport(0x3ce,mask | 0x0008);
            for(i=1; i<bwidth; ++i) {

/* Next byte */
                mask = (0xffff << left) & 0xff00;
                mask |= (sp[i]<<8);
                outport(0x3ce,mask | 0x0008);

sp[i] = fg;
            }

/* Last byte */
            mask = end_mask (sp[bwidth]<<8);
            outport(0x3ce,mask | 0x0008);

sp[bwidth] = fg;

sp += screen_params.lbytes;
        }
    }
    outport(0x3ce,0x205); /* read mode 0,write
mode 2 */ return(0);
} int digit1(void)
{
    int retval = 0;

switch ( getch( )) {

/* Look for an Escape, q or Q key */
    case ESC:
    case CHAR_q:
    case CHAR_Q:
        retval = 1; /* done */
        break;
    case 0:
        kbfunc = digit2;
        retval = 0;
        break;
    case 0x38: /* fn 8 */
        /* top */
        toggle_top( );
        retval = 0;
        break;
    case 0x34: /* fn u */
```

Appendix 1-continued

```
    mask = (0xff << left) & 0xff00;
    mask |= (sp[0]<<8);
    outport(0x3ce,mask | 0x0008);

sp[0] = fg;

/* bottom */
    toggle_bottom( );
    retval = 0;
    break;

case 0x36: /* fn o */
    /* right */
    toggle_right( );
    retval = 0;
    break;

default:
    /* all off*/
    top_off( );
    left_off( );
    bottom_off( );
    right_off( );
    retval = 0;
    break;
  }
  return(retval);
}
int digit2(void)
{
  int retval = 0;

/* Look for an Escape key */
  switch (getch( )) {

/* Look for an Escape, q or Q key */
  case ESC:
  case CHAR_q:
  case CHAR_Q:
    retval = 1; /* done */
    break;
  case 0:
    /* Don't think this should ever happen */
    retval = 0;
    break;

case 0x48: /* actual up arrow key */

/* Just beep if we are going bigger than the
biggest */
    if(Cur+1 >= VNUM)
    {
      beep2( );
      break;
    } draw_rect(0, 0, screen_params.w,
screen_params.h, BG);

Cur++;
    toggle_top( );
    retval = 0;
    break;

default:
    top_off( ),
    left_off( ),
    bottom_off( ),
    right_off( ),
    retval = 0;
    break;
  }

/* always go back to other function after second
digit is received */
  kbfunc = digit1;

return(retval);
```

```
    /* left */
    toggle_left( );
    retval = 0;
    break;

case 0x32: /* fn k */ draw_chars(Cur);

toggle_top = top_on;
    toggle_left = left_on;
    toggle_bottom = bottom_on;
    toggle_right = right_on;

break;

case 0x4d: /* actual right arrow key */
case 0x44: /* f10 */
    /* right */
    toggle_right( );
    retval = 0;
    break;

case 0x4b: /* actual left arrow key */
case 0x43: /* f9 */
    /* left */
    toggle_left( );
    retval = 0;
    break;

case 0x50: /* actual down arrow key */

/* Just beep if we attempt to go smaller than
the smallest */
    if(Cur - 1 <= 0)
    {
      beep2( );
      break;
    } draw_rect(0, 0, screen_params.w,
screen_params.h, BG);
    --Cur;

draw_chars(Cur);

toggle_top = top_on;
    toggle_left = left_on;
    toggle_bottom = bottom_on;
    toggle_right = right_on;

break;

case 0x85: /* fl 1 */
    /* bottom */
    toggle_bottom( );
    retval = 0;
    break;

case0x86: /* f12 */
    /* top */
{
    draw_block(bottom, COLOR_INDEX);
    toggle_bottom = bottom_off;
    return(1);
}
int bottom_off( )
{
    draw_block(bottom, WHITE);
    toggle_bottom = bottom_on;
    return(0);
} int do_parameter(char *argv)
{
  char cred[4];
  char cgreen[4];
  char cblue[4];
  int error_condition = 0;
```

Appendix 1-continued

```
}
int top_on( )
{
    draw_block(top, COLOR_INDEX);
    toggle_top = top_off;
    return(1);
}
int top_off( )
{
    draw_block(top, WHITE);
    toggle_top = top_on;
    return(0);
}
int left_on( )
{
    draw_block(left, COLOR_INDEX);
    toggle_left = left_off;
    return(1);
}
int left_off( )
{
    draw_block(left, WHITE);
    toggle_left = left_on;
    return(0);
}
int right_on( )
{
    draw_block(right, COLOR_INDEX);
    toggle_right = right_off;
    return(1);
}
int right_off( )
{
    draw_block(right, WHITE);
    toggle_right = right_on;
    return(0);
}
int bottom_on( )
    mask = (0xff << left) & 0xff00;
    mask = mask (sp[0]<<8);
    outport(0x3ce,mask | 0x0008); /* set plane
mask, reg 8, bit map register */
    sp[0]= fg;

/* Middle byte */
    mask = 0xff00 | (sp[1]<<8);
    outport(0x3ce,mask | 0x0008); /* set plane
mask, reg 8, bit map register */
    sp[1]= fg;

/* Last byte */
    mask = end_mask | (sp[2]<<8);
    outport(0x3ce,end_mask | 0x0008); /* set
plane mask, reg 8, bit map register */
    sp[2] = fg;

sp += screen_params.lbytes;
  }
}
else {
  for(j=0;j<h,++j) {

/* First byte */
    mask = (0xff << left) & 0xffff00;
    mask |= (sp[0]<<8);
    outport(0x3ce,mask | 0x0008); /* set plane
mask, reg 8, bit map register */ sp[0]= fg;

for(i=1; i<bwidth; ++i) {

/* Next byte */
      mask = (0xffff << left) & 0xff00;
      mask |= (sp[i]<<8);
      outport(0x3ce,mask | 0x0008); /* set
plane mask, reg 8, bit map register */ sp[i] = fg;

switch(argv[0])
    {
      case 'w':
      case 'W':
        width = (int)atoi(&argv[1]);
        if(width <= 0 width >= 480)
        {
          fprintf(stderr,"illegal value for width,
%d\n",width);
          error_condition = 1;
        } top.w = width;
        top.x = 320 - (width/2);
        bottom.w = width;
        bottom.x = 320 - (width/2);
        left.h = width;
        left.y = 240 - (width/2);
        right.h = width;
        right.y = 240 - (width/2);

break;
      case 'h';
      case 'H':
        height = (int)atoi(&argv[1]);
        if(height <= 0 || height >= 480)
        {
          fprintf(stderr,"illegal value for height,
%d\n",height);
          error_condition = 1;
        } top.h = height;
        top.y = 0;
        bottom.h = height;
        bottom.y = 480 - height;
        left.w = height;
        return(0);
}
void draw_E(int v, int x0, int y0)
{
    int width = (int)( shapes[v].wd - shapes[v].x1);
    int x1 = x0 + shapes[v].x1;

draw_rect(x0,y0,shapes[v].uw,shapes[v].ht,FG);
    draw_rect(x1,y0,width,shapes[v].uw,FG);

draw_rect(x1,y0+shapes[v].y2,width,shapes[v].uw,
FG);

draw_rect(x1,y0+shapes[v].y4,width,shapes[v].uw,
FG);
}
void draw_F(int v, int x0, int y0)
{
    int width = (int)( shapes[v].wd - shapes[v].x1 );
    int x1 = x0 + shapes[v].x1;

draw_rect(x0,y0,shapes[v].uw,shapes[v].ht,FG);
    draw_rect(x1,y0,width,shapes[v].uw,FG);
    draw_rect(x1,y0+shapes[v].y2,width-
shapes[v].uw,shapes[v].uw,FG);
} void draw_H(int v, int x0, int y0)
{
    int width = (int)( shapes[v].x4 - shapes[v].x1);

draw_rect(x0,y0,shapes[v].uw,shapes[v].ht,FG);
    draw_rect(x0+shapes[v].x1,
        y0+shapes[v].y2,
        width,
        shapes[v].uw,FG);

draw_rect(x0+shapes[v].x4,y0,shapes[v].uw,shapes
[v].ht,FG);
}
```

Appendix 1-continued

```
        }

/* Last byte */
    mask = end_mask | (sp[bwidth]<<8);
    outport(0x3ce,mask | 0x0008); /* set plane
mask, reg 8, bit map register */ sp[bwidth] = fg;

sp += screen_params.lbytes;
      }
    }
  outport(0x3ce,0x205); /* read mode 0,write
mode 2 */ left.x = 0;
    right.w = height;
    right.x = 640 - height;

break;
  case 'o':
  case 'O':
    offset == (int)atoi(&argv[1]);
    if( offset >= 480)
    {
        fprintf(stderr,"illegal value for offset,
%d\n;",offset);
        error_condition = 1;
    }
    break;
  case 'c':
  case 'C':
    strncpy(cred,&argv[1],3);
    cred[3]= '\000';
    strncpy(cgreen,&argv[4],3);
    cgreen[3] = '\000';
    strncpy(cblue,&argv[7],3);
    cblue[3] = '\000';
    red = (int)atoi(cred);
    green = (int)atoi(cgreen);
    blue = (int)atoi(cblue);
    if(red > 255)
    {
        fprintf(stderr,"illegal value for red,
%d\n",red);
        error_condition = 1;
    }
    if(green >255)
    {
        fprintf(stderr,"illegal value for green,
%d\n",green);
        error_condition = 1;
    }
    if(blue > 255)
    {
        fprintf(stderr,"illegal value for blue,
%d\n",blue);
        error_condition = 1;
    }
    break;
  }
  return error_condition;
}
int draw_rect(int x, int y, int w, int h, u_char fg)
{
  u_short end,mask end_mask;
  u_short ybyte = y*screen_params.lbytes;
  u_short sbyte = ybyte + (x>>3);
  u_short ebyte = ybyte + ((x+w-1)>>3);
    draw_rect(x0+shapes[v].x2, y0+shapes[v].uw,
shapes[v].uw,
         shapes[v].ht - shapes[v].uw,FG);
}
void init_shapes(void)
{
  int i,j,chars = 5;
  int w;
  float width,cx,cy;

void draw_L(int v, int x0, int y0)
{
  int width = (int)( shapes[v].wd - shapes[v].x1 );

draw_rect(x0,y0,shapes[v].uw,shapes[v].ht,FG);

draw_rect(x0+shapes[v].x1,y0+shapes[v].y4,width,
shapes[v].uw,FG);
} void draw_T(int v, int x0, int y0)
{
  int unit = (int)(2.0*shapes[v].ut);

draw_rect(x0,y0,shapes[v].wd,shapes[v].uw,FG);
  u_short bwidth = ebyte - sbyte;
  u_char left = 8 - (x & 7); /* (data >> count) <<8
*/
  u_char *sp = (u_char *)screen_params.addr +
sbyte;
  u_short color_compare = (fg << 8) | 0x02;
  int i,j;

end = (x+w) & 7;
  if(end = 0)
      end_mask = 0xff00;
  else
      end_mask = 0xff00 << (8-end);

outport(0x3ce,0xff07); /* color dont care - we
care all 4 planes */
  outport(0x3ce,color_compare);
  outport(0x3ce,0xa05); /* read mode 1,write
mode 2(page 111 PC Video Systems */
  outport(0x3ce,0x003); /* rotate, raster op */ if(bwidth == 0) { for(j=0j<h;++j) {
      mask = (0xff00 >> (x&7)) & 0xff00;
      mask = (mask & end_mask) | (sp[0]<<8);
      outport(0x3ce,mask | 0x0008); /* set plane
mask, reg 8, bit map register */
      sp[0]= fg;
      sp += screen_params.lbytes;
    }
  }
  else if(bwidth == 1) { for(j=0;j<h;++j) {

/* First byte */
      mask = (0xff << left) & 0xff00;
      mask |= (sp[0]<<8);
      outport(0x3ce,mask | 0x0008); /* set plane
mask, reg 8, bit map register */
      sp[0] = fg;

/* Last byte */
      mask = end_mask | (sp[1]<<8);
      outport(0x3ce,mask 0x0008); | 0x0008); /* set plane
mask, reg 8, bit map register */
      sp[1] = fg;
      sp += screen_)params.lbytes;
    }
  }
  else if(bwidth == 2) {
    for(j=0j<h;++j) {

/* First byte */
  int chars = 5;
  int h = shapes[v].ht;
  int inc = 2*shapes[v].wd;
  int x = (screen_params.w/2) - (shapes[v].1w/2);
  int y = (screen_params.h/2) - (h/2);
  int i;
  void (*draw_func[6]( );

draw_func[0] = draw_E;
```

Appendix 1-continued

```
    for(i=0;i<VNUM;++i)
    {
      width = 4.0*heights[i] /5.0;
      cx = width/2.0;
      cy = heights[i]/2.0;
      shapes[i].ht = (int) (heights[i] + 0.04);
      shapes[i].wd = (int) (width + 0.04);
      shapes[i].ut = shapes[i].ht/10.0;
      shapes[i].uw = (int) (2.0 * shapes[i].ut + 0.05
); /* round up */
      shapes[i].cx = (int) (cx + 0.2);
      shapes[i].cy = (int) (cy); /* round down */
      shapes[i].x1 = (int) ( shapes[i].ut * 2.0);
      shapes[i].x2 = (int) ( shapes[i].cx -
(shapes[i].uw/2));
      shapes[i].x3 = (int) (shapes[i].cx +
(shapes[i].uw/2));
      shapes[i].x4 = (int) (width - (shapes[i].ut * 2.0)
);
      shapes[i].y1 = (int) ( shapes[i].ut * 2.0);
      shapes[i].y2 = (int) ( shapes[i].cy -
((shapes[i].uw+1)/2) );
      shapes[i].y3 = (int) (shapes[i].cy +
(shapes[i].uw/2));
      shapes[i].y4 = (int) ( shapes[i] .ht - shapes[i].uw
);

/* Determine how many chars can fit on the
screen */
      for(j=chars; j>0,; --j)
      {
        w =j*shapes[i].wd + (j - 1)*shapes[i].wd;

if( w < screen_params.w -
(screen_params.w/8))
        {
          shapes[i].chars = j;
          shapes[i].lw = w;
          break;
        }
      }
    }
}
void draw_chars( int v)
{
rgb[2].blue = (unsigned char)(blue/4);
for(k=3 ;k<16;++k) {
  rgb[k].red = 0;
  rgb[k].green = 0;
  rgb[k].blue = 0;
}
clrtbl[0] = 0;
clrtbl[1] = 1;
clrtbl[2] = 2;
clrtbl[3] = 3;
clrtbl[4] = 4;
clrtbl[5] = 5;
clrtbl[6] = 6;
clrtbl[7] = 7;
clrtbl[8] = 8;
clrtbl[9] = 9;
clrtbl[10] = 10;
clrtbl[11] = 11;
clrtbl[12] = 12;
clrtbl[13] = 13;
clrtbl[14] = 14;
clrtbl[15] = 15;
clrtbl[16] = 1; /* overscan black */
top.y += offset;
bottom.y -= offset;
left.x += offset;
right.x -= offset;
setbmode(screen_params.mode);
setpall((unsigned char far *)rgb);
setpall 6(clrtbl);
init_shapes( );
kbfunc = digit1;
toggle_top = top_on;

draw_func[1] = draw_F;
      draw_func[2] = draw_H;
      draw_func[3] = draw_L;
      draw_func[4] = draw_T;
      draw_func[5] = (void *)0;

for(i=0;i<shapes[v].chars;++i)
      {
        if(draw_func[i] = (void *)0)
          break;

draw_func[i](v, x, y);
        x += inc;
      }
}
void main(int argc,char **argv)
{
  char tmp[64];
  int k;
  int i;
  int error = 0;

for(i=0;argv[i];++i)
  {
    if(argv[i][0]=='-'|| argv[i][0]=='/')
    {
      error += do_parameter(&argv[i][1]);
    }
  }
  if(error)
    exit(0);

#if 0
    printf("width = %d height = %d offset = %d red
= %d green = %d blue = %d\n",
        width,height,offset,red,green,blue);
endif getbmode(&mode);

rgb[0].red = 63; rgb[0].green = 63; rgb[0].blue
= 63; /* [0]white */
    rgb[1].red = 0; rgb[1].green = 0; rgb[1].blue =
0;/* [1] black*/
    rgb[2].red = (unsigned char)(red/4);
    rgb[2].green = (unsigned char)(green/4);
```

Appendix 1-continued

```
toggle_left = left_on;
toggle_bottom = bottom_on;
toggle_right = right_on;
draw_chars(Cur);
while(1) {
  if(kbhito( )){
    if( kbfunc( ))
      break;
  }
}
setbmode(mode.mode);
}
```

I claim:

1. An apparatus for communicating to and vision testing of a deaf or severely hearing-impaired examinee by an examiner comprising:
   a) a display device for displaying visual acuity testing targets;
   b) a plurality of indicator lights compromising individually energizable light-emitting means juxtaposed along a parallel line of sight of said examinee as said display device and equidistant from the examinee as said display device;
   c) means for selectively controlling activation of each said light-emitting means to indicate messages for communicating to said examinee from the examiner.

2. Apparatus as in claim 1 wherein said display device for displaying visual acuity testing targets includes means for reflecting light projected from a visual acuity target projector.

3. Apparatus as in claim 1 wherein said display device for displaying visual acuity testing targets includes a device having a surface imprinted with said visual acuity testing targets.

4. Apparatus as in claim 1 wherein said display device for displaying visual acuity testing targets includes:
   a) said targets imprinted upon a panel of translucent material;
   b) means for illuminating said panel from the rear to permit viewing of said targets from the front.

5. Apparatus as in claim 1 wherein said indicator lights comprising individually energizable light emitting means emit identical wavelength light.

6. Apparatus as in claim 1 wherein said indicator lights comprising individually energizable light emitting means emit light having a plurality of wavelengths.

7. Apparatus as in claim 1 wherein said display device for displaying visual acuity targets includes:
   a) an electronic display;
   b) an electronic memory and processor connected to said display device having means to generate visual acuity targets on said display device;
   c) means connected to said memory and processor to control the presentation of the targets.

8. Apparatus as in claim 7 further comprising:
   a) said electronic memory and processor containing means to generate said indicator lights on said electronic display;
   b) means connected to said memory and processor to selectively activate said indicator lights.

9. A method for communicating from an examiner to a deaf or severely hearing-impaired examinee during a vision examination comprising the steps of:
   a) selectively activating a plurality of indicator lights comprising individually energizable light-emitting means juxtaposed adjacent to a display of visual acuity test targets for the purpose of communicating messages to said examinee from said examiner;
   b) simultaneously operating a refractor positioned in front of said examinee, said refractor comprising lenses and instruments for determining a current visual state of said examinee.

* * * * *